US008992825B2

(12) United States Patent
Li et al.

(10) Patent No.: US 8,992,825 B2
(45) Date of Patent: Mar. 31, 2015

(54) RAPID MANUFACTURING OF POROUS METAL PROSTHESES

(75) Inventors: Jia Li, Warsaw, IN (US); Adam M. Griner, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 196 days.

(21) Appl. No.: 13/486,310

(22) Filed: Jun. 1, 2012

(65) Prior Publication Data

US 2013/0018483 A1   Jan. 17, 2013

Related U.S. Application Data

(60) Provisional application No. 61/507,151, filed on Jul. 13, 2011.

(51) Int. Cl.
| | |
|---|---|
| *B22F 3/11* | (2006.01) |
| *B22F 3/105* | (2006.01) |
| *A61L 27/04* | (2006.01) |
| *A61L 27/56* | (2006.01) |

(52) U.S. Cl.
CPC . *A61L 27/04* (2013.01); *B22F 3/11* (2013.01); *A61L 27/56* (2013.01)
USPC ........................ 419/2; 419/8; 419/9; 427/2.24

(58) Field of Classification Search
CPC ............. B22F 2998/00; B22F 2998/10; B22F 3/1266; B22F 1/0048; B22F 2201/20; B22F 7/004; A61L 27/56; A61L 27/04
USPC ............................... 419/7–9, 39–40; 427/2.24
See application file for complete search history.

(56) References Cited

U.S. PATENT DOCUMENTS

| | | | |
|---|---|---|---|
| 5,282,861 A | 2/1994 | Kaplan | |
| 7,578,851 B2* | 8/2009 | Dong et al. ................ | 623/22.21 |
| 7,666,522 B2 | 2/2010 | Justin et al. | |
| 2001/0001640 A1* | 5/2001 | Miller et al. ..................... | 419/9 |
| 2004/0243133 A1 | 12/2004 | Materna | |
| 2007/0287027 A1 | 12/2007 | Justin et al. | |

FOREIGN PATENT DOCUMENTS

WO    WO-2013009408 A1    1/2013

OTHER PUBLICATIONS

"International Application Serial No. PCT/US2012/040395, International Preliminary Report on Patentability mailed Jan. 23, 2014", 8 pgs.
"International Application Serial No. PCT/US2012/040395, International Search Report mailed Aug. 28, 2012", 4 pgs.
"International Application Serial No. PCT/US2012/040395, Written Opinion mailed Aug. 28, 2012", 7 pgs.

* cited by examiner

*Primary Examiner* — George Wyszomierski
*Assistant Examiner* — Ngoclan T Mai
(74) *Attorney, Agent, or Firm* — Schwegman Lundberg & Woessner, P.A.

(57) ABSTRACT

An orthopaedic prosthesis and a method for rapidly manufacturing the same are provided. The orthopaedic prosthesis includes a solid bearing layer, a porous bone-ingrowth layer, and an interdigitating layer therebetween. A laser sintering technique is performed to manufacture the orthopaedic prosthesis.

18 Claims, 8 Drawing Sheets

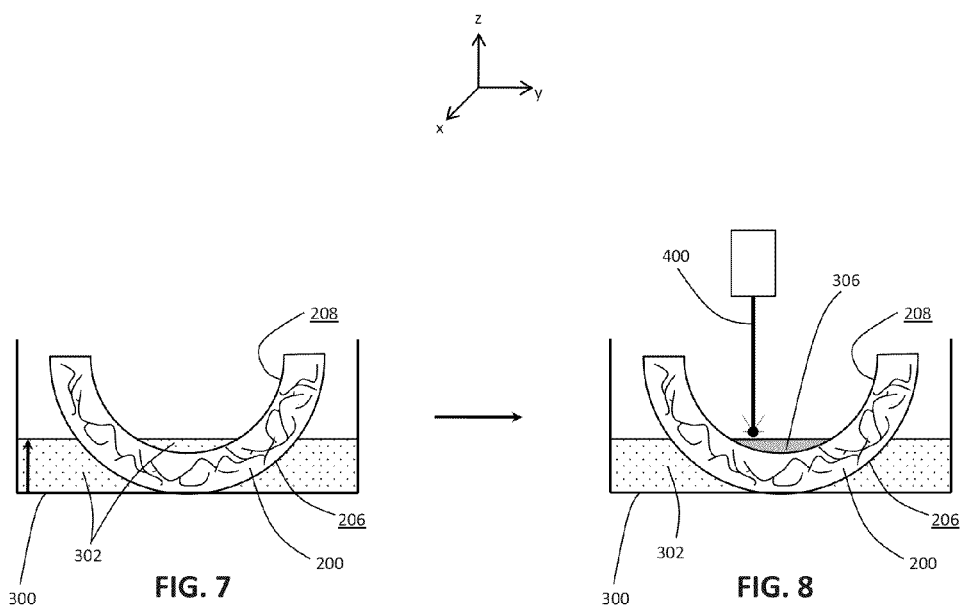

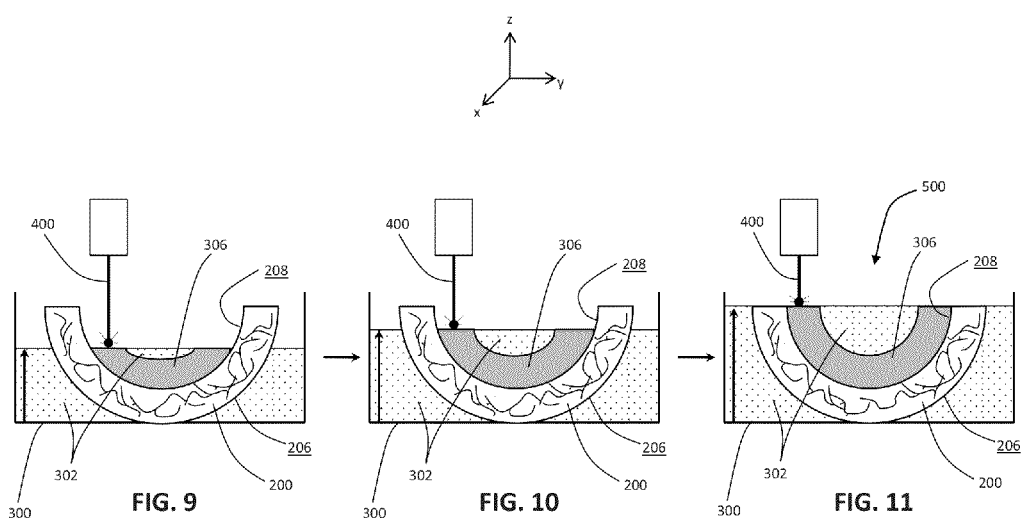

US 8,992,825 B2

RAPID MANUFACTURING OF POROUS METAL PROSTHESES

CROSS REFERENCE TO RELATED APPLICATION

This application claims priority from U.S. Provisional Patent Application Ser. No. 61/507,151, filed Jul. 13, 2011, the disclosure of which is hereby expressly incorporated by reference herein in its entirety.

FIELD OF THE DISCLOSURE

The present disclosure relates to porous metal prostheses. More particularly, the present disclosure relates to rapid manufacturing of porous metal prostheses.

BACKGROUND OF THE DISCLOSURE

Orthopaedic prostheses are commonly used to replace at least a portion of a patient's bone following traumatic injury or deterioration due to aging, illness, or disease, for example.

When the orthopaedic prosthesis is implanted into a joint, the orthopaedic prosthesis may be configured to articulate with an adjacent orthopaedic component. For example, when the orthopaedic prosthesis is implanted into the patient's hip joint, the orthopaedic prosthesis may be socket-shaped to receive and articulate with an adjacent femoral component.

The orthopaedic prosthesis may be at least partially porous to promote ingrowth of the patient's surrounding bone and/or soft tissue, which may enhance the fixation between the orthopaedic prosthesis and the patient's surrounding bone and/or soft tissue. Typically, the porous portion of the orthopaedic prosthesis is attached to a solid component, such as by diffusion bonding. Diffusion bonding, however, requires a significant amount of time to complete and subjects the orthopaedic prosthesis to high temperatures.

SUMMARY

The present disclosure provides an orthopaedic prosthesis having a solid bearing layer, a porous bone-ingrowth layer, and an interdigitating layer therebetween. The present disclosure also provides a method for rapidly manufacturing the orthopaedic prosthesis, such as by performing a laser sintering process.

According to an embodiment of the present disclosure, a method is provided for rapidly manufacturing an orthopaedic prosthesis. The orthopaedic prosthesis has a porous substrate, the porous substrate including an outer surface and a plurality of ligaments that define pores beneath the outer surface. The method includes the steps of: depositing a plurality of metal powder particles onto the outer surface of the porous substrate; allowing at least a first portion of the plurality of metal powder particles to enter the pores beneath the outer surface of the porous substrate, the first portion of the plurality of metal powder particles being sized to fit within the pores of the porous substrate; and applying an energy source to the first portion of the plurality of metal powder particles to form solid metal, the solid metal interdigitating into the pores of the porous substrate.

According to another embodiment of the present disclosure, a method is provided for rapidly manufacturing an orthopaedic prosthesis. The orthopaedic prosthesis has a solid metal component and a porous metal component, the porous metal component including a plurality of ligaments that define pores. The method includes the steps of: depositing a plurality of metal powder particles into the pores of the porous metal component; and directing an energy source into the pores of the porous metal component to convert the plurality of metal powder particles in the pores to solid metal in the pores, the solid metal in the pores coupling the solid metal component to the porous metal component.

According to yet another embodiment of the present disclosure, an orthopaedic prosthesis is provided including a solid metal layer having a first thickness, a porous metal layer having a second thickness that is less than or equal to the first thickness, the porous metal layer including a plurality of ligaments that define pores, and an interdigitating layer having a third thickness, the interdigitating layer including a plurality of ligaments that define pores, the pores of the interdigitating layer being substantially filled with solid metal, the interdigitating layer extending between the solid metal layer and the porous metal layer to couple the solid metal layer to the porous metal layer.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein:

FIG. 7 is another schematic diagram showing a third layer of metal powder deposited into and atop the porous substrate of FIG. 6;

FIG. 8 is another schematic diagram showing the laser selectively converting the third layer of metal powder of FIG. 7 to solid metal;

FIGS. 9-11 are schematic diagrams similar to FIG. 8, further showing the laser selectively converting additional layers of metal powder to solid metal to produce an orthopaedic prosthesis;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
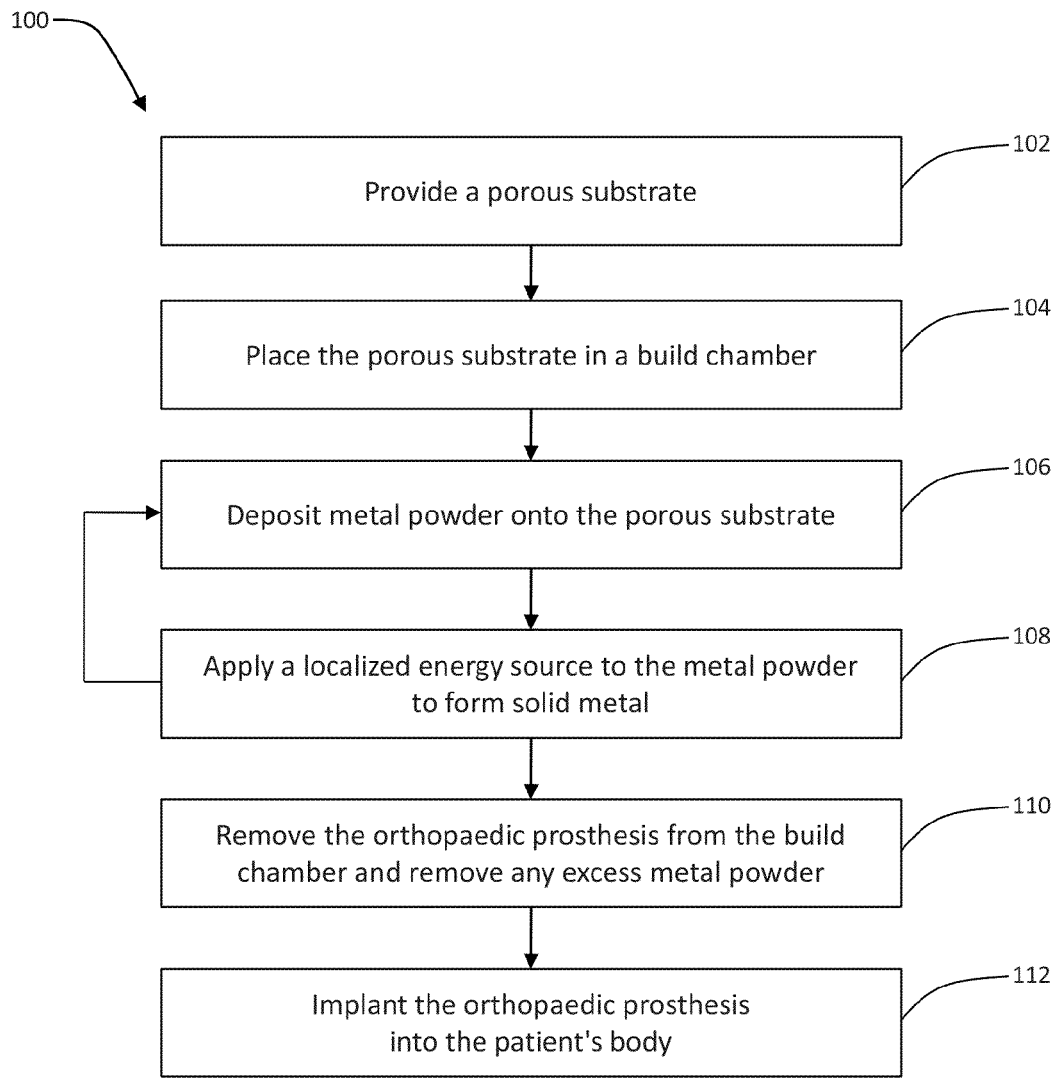
FIG. 1 is a flow chart of an exemplary method for rapidly manufacturing an orthopaedic prosthesis.

FIG. 1 provides an exemplary method 100 for designing and manufacturing an orthopaedic prosthesis. Method 100 is exemplified with reference to FIGS. 2-7.

Figure 2:
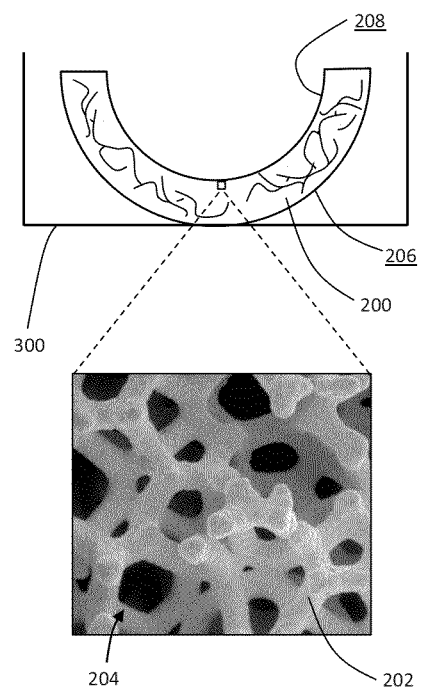
FIG. 2 is a schematic diagram of a porous substrate located within a build chamber.

Beginning at step 102 of method 100 (FIG. 1), a porous substrate 200 is provided having a large plurality of struts or ligaments 202 that define open spaces or pores 204 therebetween, as shown in FIG. 2. Ligaments 202 may be constructed, at least in part, of a first biocompatible metal, such as tantalum, a tantalum alloy, niobium, a niobium alloy, or another suitable metal, for example. In an exemplary porous substrate 200, pores 204 between ligaments 202 form a matrix of continuous channels having no dead ends, such that growth of cancellous bone and/or soft tissue through porous substrate 200 is uninhibited. Thus, porous substrate 200 may provide a matrix into which cancellous bone and/or soft tissue may grow to provide fixation of porous substrate 200 to the patient's bone.

According to an exemplary embodiment of the present disclosure, porous substrate 200 is a highly porous biomaterial having a porosity as low as 55%, 65%, or 75% or as high as 80%, 85%, or 90%. An example of such a material is produced using Trabecular Metal™ Technology generally available from Zimmer, Inc., of Warsaw, Ind. Trabecular Metal™ is a trademark of Zimmer, Inc. Porous substrate 200 may be formed from a reticulated vitreous carbon foam substrate which is infiltrated and coated with the above-described first biocompatible metal (e.g., tantalum) by a chemical vapor deposition ("CVD") process in the manner disclosed in detail in U.S. Pat. No. 5,282,861 to Kaplan, entitled "Open Cell Tantalum Structures for Cancellous Bone Implants and Cell and Tissue Receptors," filed Mar. 11, 1992, the entire disclosure of which is expressly incorporated herein by reference. By performing this CVD process, each ligament 202 of porous substrate 200 includes a carbon core covered by a thin film of the first biocompatible metal (e.g., tantalum). It is also within the scope of the present disclosure that porous substrate 200 may be in the form of a fiber metal pad, for example, the ligaments of the fiber metal pad being constructed entirely or substantially entirely of the first biocompatible metal.

Porous substrate 200 may be fabricated to virtually any desired porosity and pore size in order to selectively tailor porous substrate 200 for a particular application, as discussed in the above-incorporated U.S. Pat. No. 5,282,861. In an exemplary embodiment, porous substrate 200 has an average pore size between 100 micrometers and 1,000 micrometers, and more specifically about 500 micrometers.

During the providing step 102 of method 100 (FIG. 1), porous substrate 200 may be in a desired shape and size that is suitable for implantation in a patient's body. For example, the illustrative porous substrate 200 of FIG. 2 is provided in a hollow hemispherical shape and in a size that is suitable for implantation as an acetabular shell in a patient's hip joint. However, it is also within the scope of the present disclosure that porous substrate 200 may require subsequent shaping or machining after the providing step 102 of method 100 (FIG. 1) and before being implanted in the patient's body. Although the illustrative porous substrate 200 of FIG. 2 is shaped and sized for use as an acetabular shell in the patient's hip joint, it is also within the scope of the present disclosure that the porous substrate may be shaped and sized for use as a femoral component, a tibial component, a humeral component, a spinal component, a dental component, or another orthopaedic component, for example.

Figure 13:
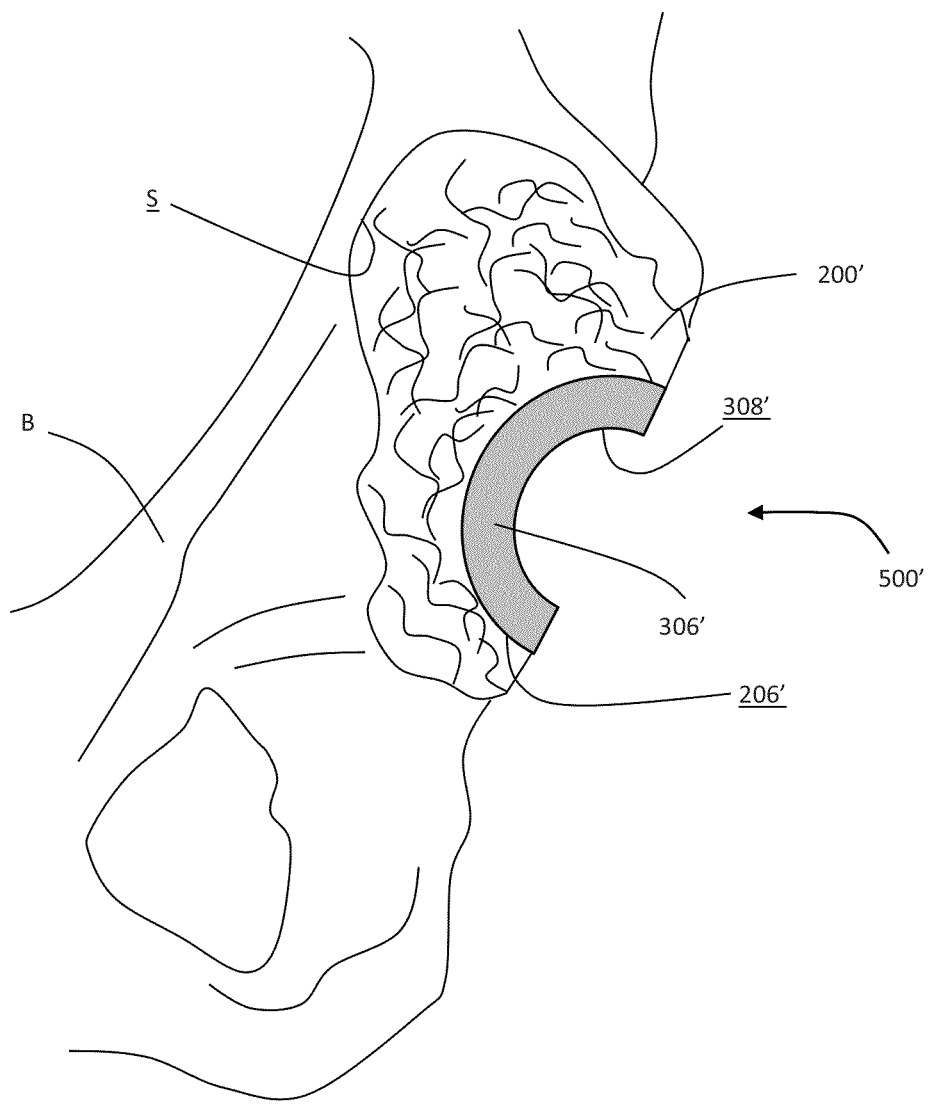
FIG. 13 is a schematic diagram of another, patient-specific orthopaedic prosthesis shown implanted in a patient's bone.

Porous substrate 200 includes a first, bone-engaging surface 206 that interacts with the patient's bone. In the illustrated embodiment of FIG. 2, the bone-engaging surface 206 of porous substrate 200 is a regular, stock surface that is shaped to interact with a prepared (e.g., reamed, cut, etc.) bone surface of a patient. In the illustrated embodiment of FIG. 13, on the other hand, the bone-engaging surface 206' of porous substrate 200' is a patient-specific surface that is shaped as substantially a negative of the particular patient's bone surface S to conform to the particular patient's bone surface S, even without preparing (e.g., reaming, cutting, etc.) the patient's bone B. The patient-specific bone-engaging surface 206' may be designed to be highly irregular, arbitrary, non-parametric, or biologically complex in shape to fill a void or defect in the particular patient's bone B and to accommodate the surrounding anatomy of the particular patient. An exemplary method of manufacturing such a patient-specific component is described in U.S. patent application Ser. No. 13/464,069 to Li et al., entitled "Patient-Specific Manufacturing of Porous Metal Prostheses," filed May 4, 2012, the entire disclosure of which is expressly incorporated herein by reference.

Porous substrate 200 also includes a second, solid-receiving surface 208. In the illustrated embodiment of FIG. 2, solid-receiving surface 208 is concave in shape and opposes bone-engaging surface 206 of porous substrate 200.

Continuing to step 104 of method 100 (FIG. 1), porous substrate 200 is placed inside a build chamber 300, as shown in FIG. 2. Build chamber 300 may be evacuated and flushed with an inert gas (e.g., argon) to avoid oxidation. Build chamber 300 may also be heated to improve the efficiency of the remaining process steps.

Figures 3, 4:
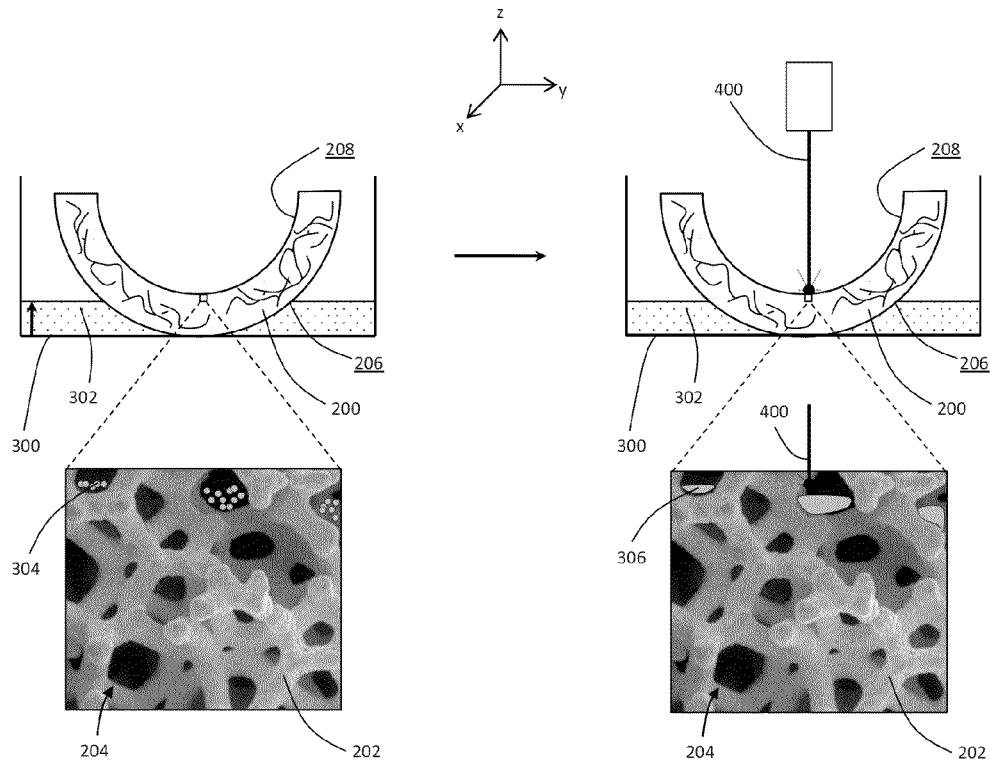
FIG. 3 is another schematic diagram showing a first layer of metal powder deposited into the porous substrate of FIG. 2.
FIG. 4 is another schematic diagram showing a laser selectively converting the first layer of metal powder of FIG. 3 to solid metal.

Next, in step 106 of method 100 (FIG. 1), a first layer of metal powder 302 is deposited onto porous substrate 200 in build chamber 300, as shown in FIG. 3. More specifically, the first layer of metal powder 302 is deposited onto solid-receiving surface 208 of porous substrate 200. Additionally, the first layer of metal powder 302 may be deposited around porous substrate 200 to support and stabilize porous substrate 200 in build chamber 300. In an exemplary embodiment, the first layer of metal powder 302, and each subsequent layer, is about 20 micrometers to about 30 micrometers thick. After depositing each new layer of metal powder 302 into build chamber 300, the newly deposited layer may be leveled by rolling a roller (not shown) across build chamber 300, by vibrating build chamber 300, or by another suitable leveling technique.

According to an exemplary embodiment of the present disclosure, metal powder 302 comprises a second biocompatible metal that differs from the first biocompatible metal of porous substrate 200. For example, if ligaments 202 of porous substrate 200 comprise or are coated with tantalum, particles 304 of metal powder 302 may comprise titanium or a titanium alloy (e.g., Ti-6Al-4V).

According to another exemplary embodiment of the present disclosure, particles 304 of metal powder 302 are sized smaller than pores 204 of porous substrate 200. Particles 304 of metal powder 302 may be less than about 10% the size of pores 204 of porous substrate 200. More specifically, particles 304 of metal powder 302 may be as little as about 1%, about 2%, or about 3% the size of pores 204 of porous substrate 200 and as much as about 4%, about 5%, or about 6% the size of pores 204 of porous substrate 200, or within a range defined between any pair of the foregoing values. For example, if pores 204 of porous substrate 200 are about 500 micrometers in size, each particle 304 of metal powder 302 may be as small as about 5 micrometers, 10 micrometers, or 15 micrometers in size and as large as about 20 micrometers, 25 micrometers, or 30 micrometers in size. In this embodiment, a large number of particles 304 may fall into pores 204 of porous substrate 200, especially pores 204 that are exposed along solid-receiving surface 208 of porous substrate 200, as shown in FIG. 3. The above-described leveling techniques may also encourage particles 304 to fall into pores 204 of porous substrate 200.

After the depositing step 106 of method 100, select areas of metal powder 302 are exposed to an energy source during step 108 of method 100 (FIG. 1). The applied energy source causes localized sintering or melting of particles 304 of metal powder 302, which converts select areas of metal powder 302 to solid metal 306. Each newly-formed region of solid metal 306 may bond to a previously-formed region of solid metal 306 and to porous substrate 200, as shown in FIG. 4. In this manner, solid metal 306 is selectively and rapidly formed upon porous substrate 200 while simultaneously bonding solid metal 306 to porous substrate 200.

In an exemplary embodiment, the applying step 108 of method 100 (FIG. 1) involves a direct metal laser sintering (DMLS) process, where the energy source is a focused, high-powered laser 400 (e.g., a ytterbium fiber optic laser). The DMLS process may also be referred to as a selective laser sintering (SLS) process or a selective laser melting (SLM) process. Suitable DMLS systems are commercially available from 3D Systems, Inc., of Rock Hill, S.C.

Laser 400 may be controlled using a suitable computer processor having, for example, computer-aided design (CAD) software and/or computer-aided manufacturing (CAM) software installed thereon. Such software can be used to rapidly create computer numerical control (CNC) code that will control each individual pass of laser 400 across build chamber 300. For example, as each layer of metal powder 302 is deposited into build chamber 300 (i.e., along the z-axis), the CNC code may direct laser 400 side-to-side across build chamber 300 (i.e., along the y-axis) and back-and-forth across build chamber 300 (i.e., along the x-axis). To convert select areas of metal powder 302 to solid metal 306, laser 400 may be activated at select xy-coordinates. To leave other areas of metal powder 302 as is, without forming solid metal 306, laser 400 may be deactivated at other xy-coordinates or may avoid traveling to those xy-coordinates altogether.

As shown by comparing FIGS. 3 and 4, even particles 304 of metal powder 302 that settled into pores 204 of porous substrate 200 during the depositing step 106 of method 100 (FIG. 1) may be converted to solid metal 306 during the applying step 108 of method 100 (FIG. 1). According to an exemplary embodiment of the present disclosure, the second biocompatible metal of particles 304 of metal powder 302 has a lower melting point than the first biocompatible metal of ligaments 202 of porous substrate 200. For example, if ligaments 202 of porous substrate 200 comprise or are coated with tantalum, which has a melting point above 3,000° C., particles 304 of metal powder 302 may comprise titanium or a titanium alloy (e.g., Ti-6Al-4V), which have melting points below 1,700° C. In this embodiment, even when laser 400 passes over and is absorbed by porous substrate 200, as shown in FIG. 4, the thermally-stable ligaments 202 of porous substrate 200 remain substantially intact without sintering or melting. However, when laser 400 passes over and is absorbed by particles 304 of metal powder 302, particles 304 may sinter or melt to form solid metal 306. If the melting points between the first and second biocompatible metals are sufficiently different, solid metal 306 within each pore 204 of porous substrate 200 may be able to maintain substantially the same elemental content as metal powder 302, without incorporating material from the thermally-stable ligaments 202 of porous substrate 200.

Figure 5:
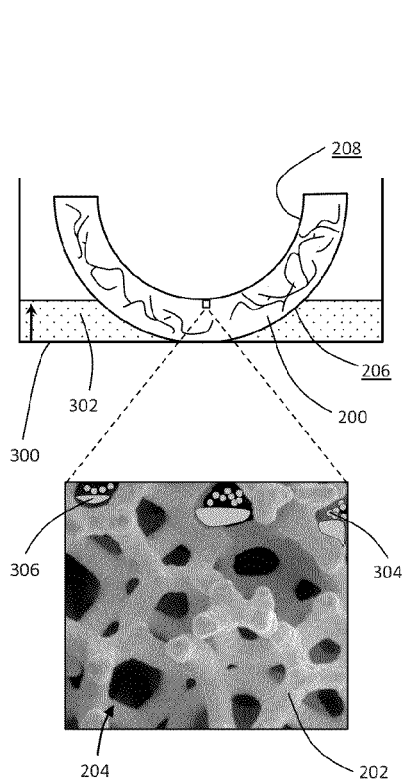
FIG. 5 is another schematic diagram showing a second layer of metal powder deposited into the porous substrate of FIG. 4.
Figure 6:
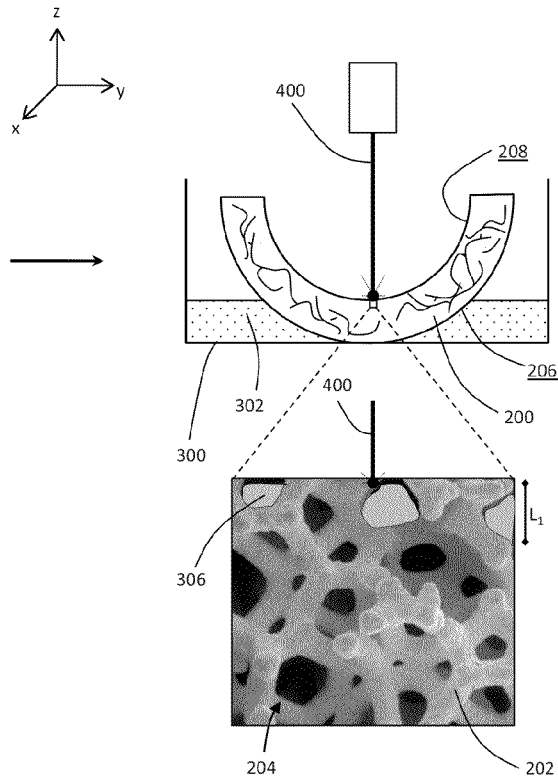
FIG. 6 is another schematic diagram showing the laser selectively converting the second layer of metal powder of FIG. 5 to solid metal.

As shown in FIGS. 5-11, the depositing step 106 and the applying step 108 of method 100 (FIG. 1) are repeated until solid metal 306 reaches a final, desired shape. As more metal powder 302 is deposited atop the previously-formed regions of solid metal 306, particles 304 of metal powder 302 begin to substantially fill the exposed pores 204 of porous substrate 200, as shown in FIG. 5. As even more metal powder 302 is deposited atop the previously-formed regions of solid metal 306, particles 304 of metal powder 302 begin to accumulate atop solid-receiving surface 208 of porous substrate 200, as shown in FIGS. 7-11. After each new layer of metal powder 302 is deposited, select areas of the newly-deposited layer are exposed to laser 400, converting more metal powder 302 to solid metal 306.

Figure 12:
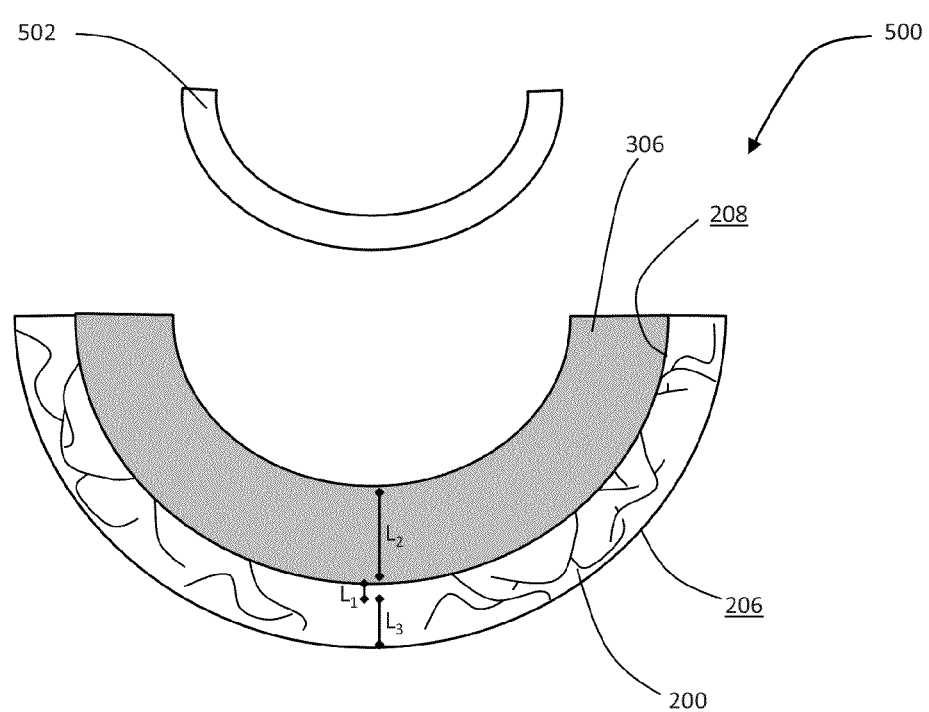
FIG. 12 is a schematic diagram of the orthopaedic prosthesis of FIG. 11, further including an exploded polymeric liner.

Together, porous substrate 200 and solid metal 306 form orthopaedic prosthesis 500 that is suitable for implantation in a patient's body. For example, the illustrative orthopaedic prosthesis 500 of FIG. 12 is suitable for implantation as an acetabular cup in a patient's hip joint. Although the illustrative orthopaedic prosthesis 500 of FIG. 12 is suitable for implantation as an acetabular cup in the patient's hip joint, it is also within the scope of the present disclosure that the orthopaedic prosthesis may be configured for implantation in a patient's femur, tibia, humerus, spine, or mouth, for example.

Returning to FIG. 6, porous substrate 200 and solid metal 306 cooperate to define an interdigitating layer $L_1$ beneath the solid-receiving surface 208 of porous substrate 200. Within the interdigitating layer $L_1$, solid metal 306 metallurgically and/or mechanically interacts with ligaments 202 of porous substrate 200 to create a strong attachment between solid metal 306 and porous substrate 200. The interdigitating layer $L_1$ may have a thickness of approximately 250 micrometers or more, 500 micrometers or more, 1,000 micrometers (1 millimeter) or more, or 1,500 micrometers (1.5 millimeters) or more, for example. Solid metal 306 in the interdigitating layer $L_1$ may be formed from particles 304 of metal powder 302 that settled into pores 204 of porous substrate 200 before exposure to laser 400, as shown in FIGS. 3-6. Additionally, solid metal 306 in the interdigitating layer $L_1$ may be formed from particles 304 of metal powder 302 that settled atop solid-receiving surface 208 of porous substrate 200 before exposure to laser 400, but that later settled into pores 204 of porous substrate 200 upon exposure to laser 400. Depending on the size of pores 204, the size of particles 304, and/or the degree to which particles 304 are heated and rendered flowable, solid metal 306 may substantially or completely fill pores 204 in the interdigitating layer $L_1$ of porous substrate 200.

In addition to the above-described interdigitating layer $L_1$, orthopaedic prosthesis 500 further includes a solid bearing layer $L_2$ and a porous bone-ingrowth layer $L_3$, as shown in FIG. 12. Solid metal 306 extends beyond porous substrate 200 and the interdigitating layer $L_1$ to form the solid bearing layer $L_2$. The solid bearing layer $L_2$ may have a thickness of approximately 0.5 inch or more, 1.0 inch or more, 1.5 inches or more, or 2.0 inches or more, for example. Porous substrate 200 extends beyond solid metal 306 and the interdigitating layer $L_1$ to define the porous bone-ingrowth layer $L_3$.

An exemplary orthopaedic prosthesis 500 is predominantly solid, not porous, by weight and/or volume. In one embodiment, the thickness of the porous bone-ingrowth layer $L_3$ is less than or equal to the thickness of the solid bearing layer $L_2$ to arrive at orthopaedic prosthesis 500 that is predominantly solid. In this exemplary embodiment, the solid bearing layer $L_2$ of orthopaedic prosthesis 500 constitutes more than just a thin surface coating on the porous bone-ingrowth layer $L_3$.

Advantageously, the above-described depositing step 106 and the above-described applying step 108 of method 100 (FIG. 1) produce orthopaedic prosthesis 500 in a rapid and automated manner. The solid bearing layer $L_2$ of orthopaedic prosthesis 500 may be rapidly and automatically manufactured to strengthen and support orthopaedic prosthesis 500 and/or to interact with an adjacent orthopaedic component. In the illustrated embodiment of FIG. 12, for example, the solid bearing layer $L_2$ of orthopaedic prosthesis 500 is configured to receive a polymeric liner 502, which in turn interacts with and receives the patient's adjacent femoral head. Also, the solid bearing layer $L_2$ of orthopaedic prosthesis 500 may be rapidly and automatically manufactured in a highly complex geometry, without requiring any subsequent shaping. At substantially the same time, the interdigitating layer $L_1$ may be rapidly and automatically produced to bond the solid bearing layer $L_2$ to the underlying porous bone-ingrowth layer $L_3$.

Continuing to step 110 of method 100 (FIG. 1), orthopaedic prosthesis 500 is removed from build chamber 300, leaving behind metal powder 302 that was not converted to solid metal 306. Also, excess metal powder 302 may be removed from porous substrate 200 by shaking orthopaedic prosthesis 500 and/or by blowing pressurized air into porous substrate 200, for example. Orthopaedic prosthesis 500 may then be subjected to any necessary cleaning, shaping, processing, sterilizing, or packaging steps. For example, in the illustrated embodiment of FIG. 12, the polymeric liner 502 may be coupled to solid bearing layer $L_2$ of orthopaedic prosthesis 500 to facilitate articulation with the patient's adjacent femoral head.

Finally, in step 112 of method 100 (FIG. 1), orthopaedic prosthesis 500 is implanted into the patient's body. Bone-engaging surface 206 of orthopaedic prosthesis 500 is implanted against the patient's bone to encourage bone and/or soft tissue ingrowth into the porous bone-ingrowth layer $L_3$ of orthopaedic prosthesis 500. Orthopaedic prosthesis 500 may be secured in place using suitable fasteners (e.g., bone screws) or bone cement, for example.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of rapidly manufacturing an orthopaedic prosthesis having a porous substrate, the porous substrate including an outer surface and a plurality of ligaments that define pores beneath the outer surface, the method comprising the steps of:
    depositing a plurality of metal powder particles onto the outer surface of the porous substrate;
    allowing at least a first portion of the plurality of metal powder particles to enter the pores beneath the outer surface of the porous substrate, the first portion of the plurality of metal powder particles being sized to fit within the pores of the porous substrate; and
    applying an energy source to the first portion of the plurality of metal powder particles to form solid metal, the solid metal interdigitating into the pores of the porous substrate.

2. The method of claim 1, wherein the energy source comprises a laser.

3. The method of claim 1, wherein a second portion of the plurality of metal powder particles is located at or beyond the outer surface of the porous substrate.

4. The method of claim 3, wherein, after the applying step, the second portion of the plurality of metal powder particles is converted to solid metal to form a solid bearing layer on the porous substrate.

5. The method of claim 1, wherein the plurality of metal powder particles comprise titanium or a titanium alloy.

6. The method of claim 1, wherein the plurality of ligaments of the porous substrate comprise tantalum.

7. The method of claim 1, wherein the pores of the porous substrate are about 500 micrometers in size.

8. The method of claim 1, wherein the plurality of metal powder particles are each less than about 30 micrometers in size.

9. The method of claim 1, wherein the porous substrate has a porosity of 55% to 90%.

10. The method of claim 9, wherein the plurality of ligaments of the porous substrate comprise tantalum.

11. The method of claim 1, wherein the porous substrate has a porosity of 65% to 85%.

12. A method of rapidly manufacturing an orthopaedic prosthesis having a solid metal component and a porous metal component, the porous metal component including a plurality of ligaments that define pores, the method comprising the steps of:
    depositing a plurality of metal powder particles into the pores of the porous metal component; and
    directing an energy source into the pores of the porous metal component to convert the plurality of metal powder particles in the pores to solid metal in the pores, the solid metal in the pores coupling the solid metal component to the porous metal component.

13. The method of claim 12, wherein the plurality of metal powder particles has a lower melting point than the plurality of ligaments of the porous metal component.

14. The method of claim 13, wherein the directing step melts the plurality of metal powder particles located in each pore without melting the plurality of ligaments that surround the pore.

15. The method of claim 12, wherein the solid metal in the pores and the solid metal component have the same elemental content.

16. The method of claim 12, wherein the porous metal component has a porosity of 55% to 90%.

17. The method of claim 16, wherein the plurality of ligaments of the porous metal component comprise tantalum.

18. The method of claim 12, wherein the porous metal component has a porosity of 65% to 85%.

* * * * *